United States Patent
Kato et al.

(10) Patent No.: US 8,183,528 B2
(45) Date of Patent: May 22, 2012

(54) ELECTROMAGNETIC WAVE MEASURING APPARATUS, MEASUREMENT METHOD, A PROGRAM, AND A RECORDING MEDIUM

(75) Inventors: Eiji Kato, Miyagi (JP); Shigeki Nishina, Miyagi (JP); Motoki Imamura, Miyagi (JP); Akiyoshi Irisawa, Miyagi (JP); Tomoyu Yamashita, Miyagi (JP)

(73) Assignee: Advantest Corporation, Tokyo (JP)

( * ) Notice: Subject to any disclaimer, the term of this patent is extended or adjusted under 35 U.S.C. 154(b) by 377 days.

(21) Appl. No.: 12/487,177

(22) Filed: Jun. 18, 2009

(65) Prior Publication Data

US 2010/0271001 A1    Oct. 28, 2010

(30) Foreign Application Priority Data

Apr. 22, 2009    (JP) ................. 2009-103784

(51) Int. Cl.
*G01R 23/16*    (2006.01)
(52) U.S. Cl. ................. 250/358.1; 250/370.06
(58) Field of Classification Search ............... 250/336.1, 250/358.1, 370.06, 339.07, 504 R
See application file for complete search history.

(56) References Cited

U.S. PATENT DOCUMENTS

| | | | |
|---|---|---|---|
| 6,873,405 B2 | 3/2005 | Kido et al. | |
| 7,099,432 B2 | 8/2006 | Ichihara et al. | |
| 7,119,339 B2 | 10/2006 | Ferguson et al. | |
| 2005/0074088 A1 | 4/2005 | Ichihara et al. | |

FOREIGN PATENT DOCUMENTS

| | | |
|---|---|---|
| JP | 2005-121633 | 5/2005 |
| JP | 3828111 | 7/2006 |

OTHER PUBLICATIONS

English language Abstract of JP 3828111, Jul. 14, 2006.
S. Wang et al., "Pulsed terahertz tomography", J. Phys. D, vol. 37 (2004), pp. R1-R36.
B. Ferguson et al., "Towards functional 3D T-ray imaging", Physics in Medicine and Biology, vol. 47, No. 21, Oct. 17, 2002, pp. 3735-3742.
B. Ferguson et al., "T-ray computed tomography", Optics Letters, vol. 27, No. 15, Aug. 1, 2002, pp. 1312-1314.
Tani et al., "4.10.4 Spectroscopic application of terahertz electromagnetic wave pulse", Ryoshi Kogaku Handbook (Quantum Engineering Handbook), [ISBN: 4-254-21031-0], Nov. 20, 1999, pp. 917-919.

*Primary Examiner* — David Porta
*Assistant Examiner* — Djura Malevic
(74) *Attorney, Agent, or Firm* — Greenblum & Bernstein, P.L.C.

(57) ABSTRACT

According to the present invention, the CT is carried out based on parameters other than the absorption rate. An electromagnetic wave measurement device includes an electromagnetic wave output device 2 which outputs an electromagnetic wave at a frequency equal to or more than 0.01 [THz] and equal to or less than 100 [THz] toward a device under test 1, an electromagnetic wave detector 4 which detects the electromagnetic wave which has transmitted through the device under test 1, a relative position changing unit 6 which changes a relative position of an intersection 100 at which an optical path of the electromagnetic wave transmitting through the device under test 1 and the device under test 1 intersect with respect to the device under test 1, a phase deriving unit 12 which derives, based on a detected result by the electromagnetic wave detector 4, a phase in the frequency domain of the electromagnetic wave which has transmitted through the device under test 1, a sinogram deriving unit 16 which derives a sinogram based on a derived result by the phase deriving unit 12, and a cross sectional image deriving unit 18 that derives, based on the sinogram, an image of a cross section of the device under test 1 including a trajectory of the intersection 100.

10 Claims, 7 Drawing Sheets

ELECTROMAGNETIC WAVE MEASURING APPARATUS, MEASUREMENT METHOD, A PROGRAM, AND A RECORDING MEDIUM

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been the computed tomography (CT) as a method for obtaining tomographic information on a device under test. This method conducted while a generator and a detector of the X ray are used is referred to as X-ray CT. With the X-ray CT, it is possible to acquire tomographic information on a human body in non-destructive and non-contact manner.

SUMMARY OF THE INVENTION

However, it is difficult for the X-ray CT to detect internal states (such as defects and distortions) of industrial products constructed by semiconductors, plastics, ceramics, woods, and papers (hereinafter referred to as "raw materials"). This is because the X-ray presents a high transmission property to any materials.

On the other hand, the terahertz wave (frequency thereof is equal to or more than 0.03 [THz], and equal to or less than 10 [THz], for example) properly transmits through the raw materials of the industrial products described above. Therefore, the CT carried out while a generator and a detector of the terahertz wave are used (hereinafter referred to as "terahertz CT") can detect internal states of the industrial products. Patent Document 1, Patent Document 2, and Non-Patent Document 1 describe the terahertz CT.

It should be noted that the CT carries out tomography based on how much the X ray fed to a device under test is absorbed (absorption rate).

(Patent Document 1) U.S. Pat. No. 7,119,339
(Patent Document 2) Japanese patent No. 3828111
(Non-Patent Document 1) S. Wang et al., "Pulsed terahertz tomography," J. Phys. D, Vol. 37 (2004), R1-R36

However, depending on the type of the device under test, it is hard for the tomography based on the absorption rate to carry out the measurement.

It is therefore an object of the present invention to carry out the CT based on parameters other than the absorption rate.

According to the present invention, an electromagnetic wave measurement device includes: an electromagnetic wave output device that outputs an electromagnetic wave at a frequency equal to or more than 0.01 [THz] and equal to or less than 100 [THz] toward a device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a phase deriving unit that derives, based on a detected result by the electromagnetic wave detector, a phase in the frequency domain of the electromagnetic wave which has transmitted through the device under test; a sinogram deriving unit that derives a sinogram based on a derived result by the phase deriving unit; and an image deriving unit that derives, based on the sinogram, an image of a cross section of the device under test including the intersection.

According to the thus constructed electromagnetic wave measurement device, an electromagnetic wave output device outputs an electromagnetic wave at a frequency equal to or more than 0.01 [THz] and equal to or less than 100 [THz] toward a device under test. An electromagnetic wave detector detects the electromagnetic wave which has transmitted through the device under test. A relative position changing unit changes a relative position of an intersection at which an optical path of the electromagnetic wave transmitting through the device under test and the device under test intersect with respect to the device under test. A phase deriving unit derives, based on a detected result by the electromagnetic wave detector, a phase in the frequency domain of the electromagnetic wave which has transmitted through the device under test. A sinogram deriving unit derives a sinogram based on a derived result by the phase deriving unit. An image deriving unit derives, based on the sinogram, an image of a cross section of the device under test including the intersection.

According to the present invention, the electromagnetic wave measurement device may include a group delay deriving unit that derives, based on the derived result by the phase deriving unit, a group delay in the frequency domain of the electromagnetic wave which has transmitted through the device under test, wherein the sinogram deriving unit derives a sinogram for the group delay.

According to the present invention, the electromagnetic wave measurement device may include a chromatic dispersion deriving unit that derives, based on the derived result by the phase deriving unit, a chromatic dispersion in the frequency domain of the electromagnetic wave which has transmitted through the device under test, wherein the sinogram deriving unit derives a sinogram for the chromatic dispersion.

According to the electromagnetic wave measurement device of the present invention, the device under test may include a first device under test and a second device under test, the electromagnetic wave measurement device including a group delay deriving unit that derives, based on the derived result by the phase deriving unit, a first group delay in the frequency domain of the electromagnetic wave which has transmitted through the first device under test, and a second group delay in the frequency domain of the electromagnetic wave which has transmitted through the second device under test, wherein the sinogram deriving unit derives a sinogram for a difference in refraction index between the first device under test and the second device under test based on a difference between the first group delay and the second group delay.

According to the electromagnetic wave measurement device of the present invention, the refraction index of the second device under test may be known; and the sinogram deriving unit may derive a sinogram for the refraction index of the first device under test based on the difference between the first group delay and the second group delay.

According to the electromagnetic wave measurement device of the present invention, the device under test may include a first device under test and a second device under test, the electromagnetic wave measurement device including a group delay deriving unit that derives, based on the derived result by the phase deriving unit, a first group delay in the frequency domain of the electromagnetic wave which has transmitted through the first device under test, and a second group delay in the frequency domain of the electromagnetic wave which has transmitted through the second device under test wherein: the sinogram deriving unit derives a first sinogram based on the first group delay and a second sinogram based on the second group delay; and the image deriving unit derives an image of a cross section of the first device under test based on the first sinogram, and an image of a cross section of the second device under test based on the second sinogram, and, as a difference between the image of the cross section of the first device under test and the image of the cross section of second device under test, derives an image representing a difference in group delay between the first device under test and the second device under test.

According to the present invention, a measurement method using an electromagnetic wave measurement device having an electromagnetic wave output device that outputs an electromagnetic wave at a frequency equal to or more than 0.01 [THz] and equal to or less than 100 [THz] toward a device under test, an electromagnetic wave detector that detects the electromagnetic wave which has transmitted through the device under test, and a relative position changing unit that changes a relative position of an intersection at which an optical path of the electromagnetic wave transmitting through the device under test and the device under test intersect with respect to the device under test, includes: a phase deriving step that derives, based on a detected result by the electromagnetic wave detector, a phase in the frequency domain of the electromagnetic wave which has transmitted through the device under test; a sinogram deriving step that derives a sinogram based on a derived result by the phase deriving step; and an image deriving step that derives, based on the sinogram, an image of a cross section of the device under test including the intersection.

The present invention is a program of instructions for execution by a computer to perform a measurement process using an electromagnetic wave measurement device having an electromagnetic wave output device that outputs an electromagnetic wave at a frequency equal to or more than 0.01 [THz] and equal to or less than 100 [THz] toward a device under test, an electromagnetic wave detector that detects the electromagnetic wave which has transmitted through the device under test, and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a sinogram deriving step that derives a sinogram based on a derived result by the phase deriving step; and an image deriving step that derives, based on the sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave at a frequency equal to or more than 0.01 [THz] and equal to or less than 100 [THz] toward a device under test, an electromagnetic wave detector that detects the electromagnetic wave which has transmitted through the device under test, and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a sinogram deriving step that derives a sinogram based on a derived result by the phase deriving step; and an image deriving step that derives, based on the sinogram, an image of a cross section of the device under test including the intersection.

BEST MODE FOR CARRYING OUT THE INVENTION

A description will now be given of embodiments of the present invention with reference to drawings.

First Embodiment

Figure 1:
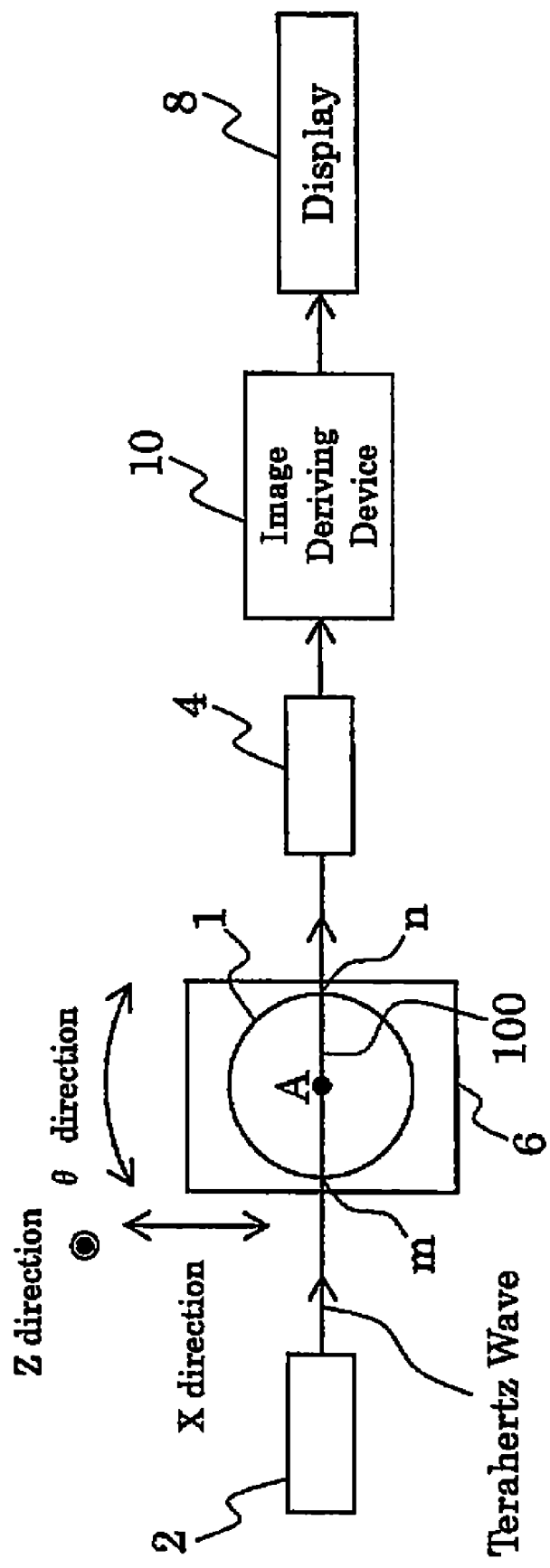
FIG. 1 is a diagram showing a configuration of an electromagnetic wave measurement device according to a first embodiment of the present invention.

FIG. 1 is a diagram showing a configuration of an electromagnetic wave measurement device according to a first embodiment of the present invention. The electromagnetic wave measurement device according to the first embodiment includes an electromagnetic wave output device 2, an electromagnetic wave detector 4, a scanning stage (relative position changing unit) 6, a display 8, and an image deriving device 10. The electromagnetic wave measurement device is used for measuring a device under test (DUT) 1.

The electromagnetic wave output device 2 outputs an electromagnetic wave at a frequency equal to or more than 0.01 [THz] and equal to or less than 100 [THz] toward the DUT 1. The frequency of the electromagnetic wave output toward the DUT 1 includes a terahertz wave band (such as equal to or more than 0.03 [THz] and equal to or less than 10 [THz]). According to the embodiment of the present invention, it is assumed to employ a terahertz wave as an example of the electromagnetic wave.

The terahertz wave output toward the DUT 1 transmits through the DUT 1. The electromagnetic wave detector 4 detects the electromagnetic wave (such as a terahertz wave) which has transmitted through the DUT 1.

A point at which the terahertz wave is made incident to the DUT 1 is m, and a point at which the terahertz wave is emitted from the DUT 1 is n. Then, an intersection 100 between an optical path of the electromagnetic wave which transmits through the DUT 1 and the DUT 1 is represented as a line mn.

Moreover, the shape of the DUT 1 viewed from above is a circle, and the center of the circle is a point A.

It should be noted that all points m1, m2, m3 and m4 are points at which the terahertz wave enters the DUT 1. All points n1, n2, n3 and n4 are points at which the terahertz wave exits from the DUT 1.

The scanning stage (relative position changing unit) 6 changes a relative position of the intersection 100 with respect to the DUT 1. For example, the DUT 1 is fixed to the scanning stage 6, the scanning stage 6 moves in the X direction and the Z direction (direction perpendicular to the sheet of FIG. 1), and rotates about a line which transmits through the point A and is perpendicular to the sheet of FIG. 1 (referred to as "movement in a θ direction").

Figure 2:
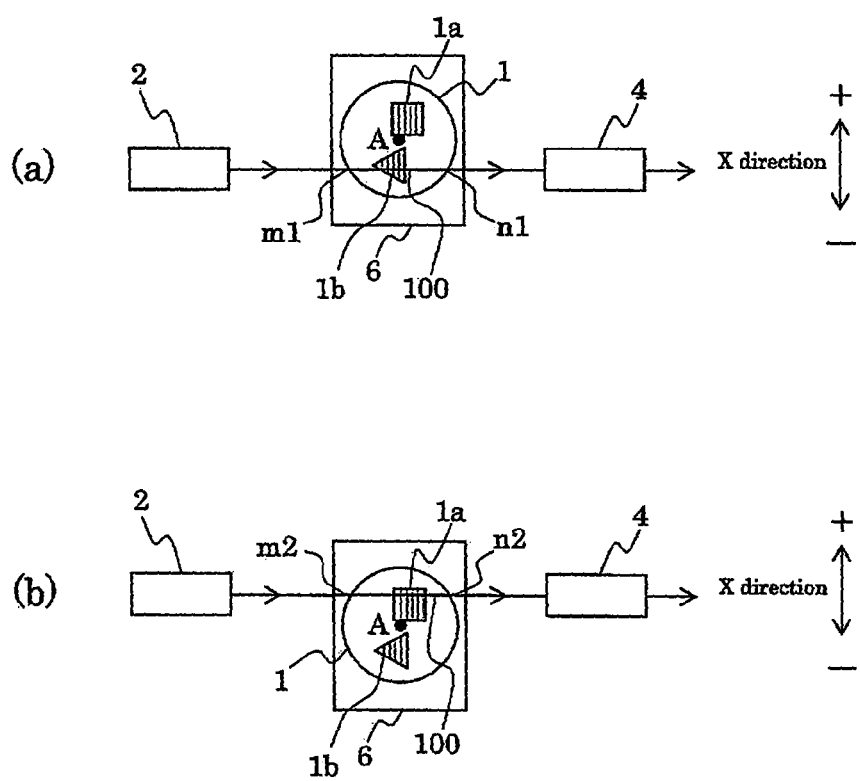
FIGS. 2(a) and 2(b) are plan views of the DUT 1, the electromagnetic wave output device 2, the electromagnetic wave detector 4, and the scanning stage 6, when the scanning stage 6 is moved in the X direction.

FIGS. 2(a) and 2(b) are plan views of the DUT 1, the electromagnetic wave output device 2, the electromagnetic wave detector 4, and the scanning stage 6, when the scanning stage 6 is moved in the X direction. It should be noted that the DUT 1 contains contents 1a and 1b.

Referring to FIG. 2(a), when the scanning stage 6 is moved in the +X direction from the state shown in FIG. 1 (alternatively, the electromagnetic wave output device 2 and the electromagnetic wave detector 4 may be moved in the −X direction), the intersection 100 is represented by a line m1n1. The relative position of the intersection 100 with respect to the DUT 1 is below the point A. The intersection 100 transmits through the content 1b.

Referring to FIG. 2(b), when the scanning stage 6 is moved in the −X direction from the state shown in FIG. 1 (alternatively, the electromagnetic wave output device 2 and the electromagnetic wave detector 4 may be moved in the +X direction), the intersection 100 is represented by a line m2n2. The relative position of the intersection 100 with respect to the DUT 1 is above the point A. The intersection 100 transmits through the content 1a.

When the scanning stage 6 is moved in the X direction, thereby changing the state from that shown in FIG. 2(a) to that shown in FIG. 2(b), the relative position of the intersection 100 with respect to the DUT 1 changes from that below the point A to that above the point A.

Figure 3:
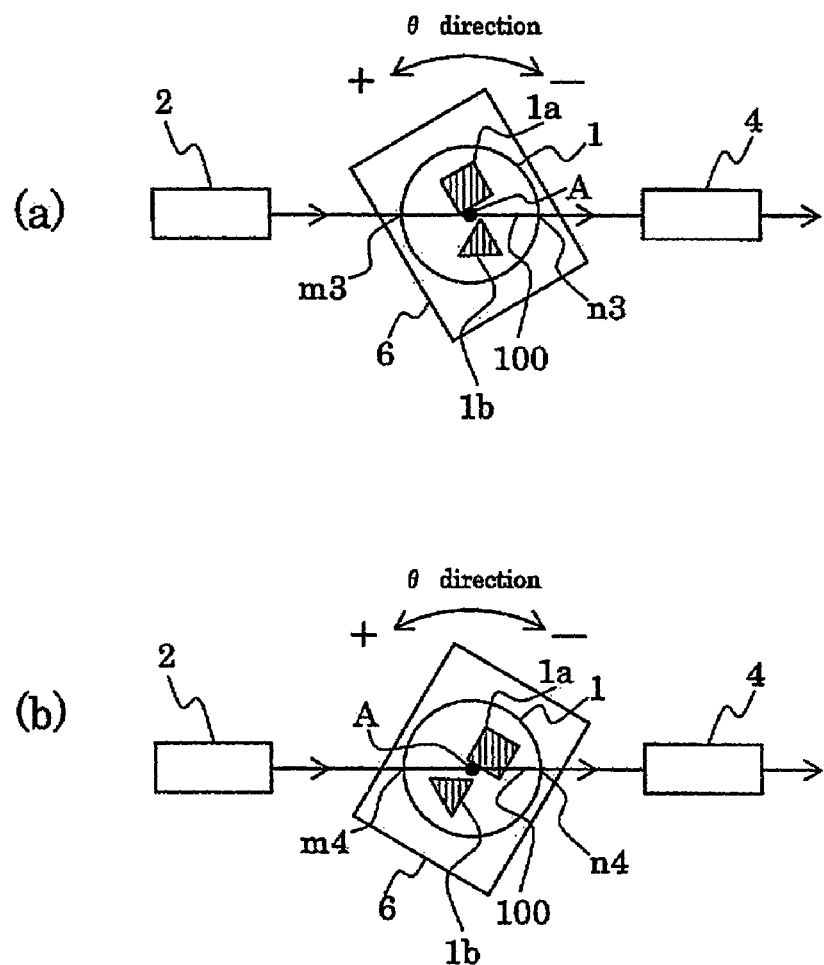
FIGS. 3(a) and 3(b) are plan views of the DUT 1, the electromagnetic wave output device 2, the electromagnetic wave detector 4, and the scanning stage 6, when the scanning stage 6 is moved in the θ direction.

FIGS. 3(a) and 3(b) are plan views of the DUT 1, the electromagnetic wave output device 2, the electromagnetic wave detector 4, and the scanning stage 6, when the scanning stage 6 is moved in the θ direction. It should be noted that the DUT 1 contains the contents 1a and 1b.

Referring to FIG. 3(a), when the scanning stage 6 is moved in the +θ direction from the state shown in FIG. 1 (alternatively, the electromagnetic wave output device 2 and the electromagnetic wave detector 4 may be moved in the −θ direction), the intersection 100 is represented by a line m3n3. The intersection 100 passes between the content 1a and the content 1b.

Referring to FIG. 3(b), when the scanning stage 6 is moved in the −θ direction from the state shown in FIG. 1 (alternatively, the electromagnetic wave output device 2 and the electromagnetic wave detector 4 may be moved in the +θ direction), the intersection 100 is represented by a line m4n4. The intersection 100 transmits through the content 1a.

When the scanning stage 6 is moved in the θ direction, thereby changing the state from that shown in FIG. 3(a) to that shown in FIG. 3(b), the relative position of the intersection 100 with respect to the DUT 1 changes.

As described above, the DUT 1 can be scanned by the scanning stage 6.

The image deriving device 10 derives an image of a cross section of the DUT 1 made on a plane containing the intersection 100 (the sheet in FIGS. 1, 2(a), 2(b), 3(a) and 3(b)).

The display 8 shows an image F(x,y) (refer to an equation (5)) derived by the image deriving device 10. The derived image is numerical data on the two-dimensional cross section of the DUT 1, and a two-dimensional cross sectional image of the DUT 1 is shown by associating the numerical data with predetermined colors. It should be noted that a widely known method may be properly employed for the method for displaying a two-dimensional cross sectional image based on numerical data.

Figure 4:
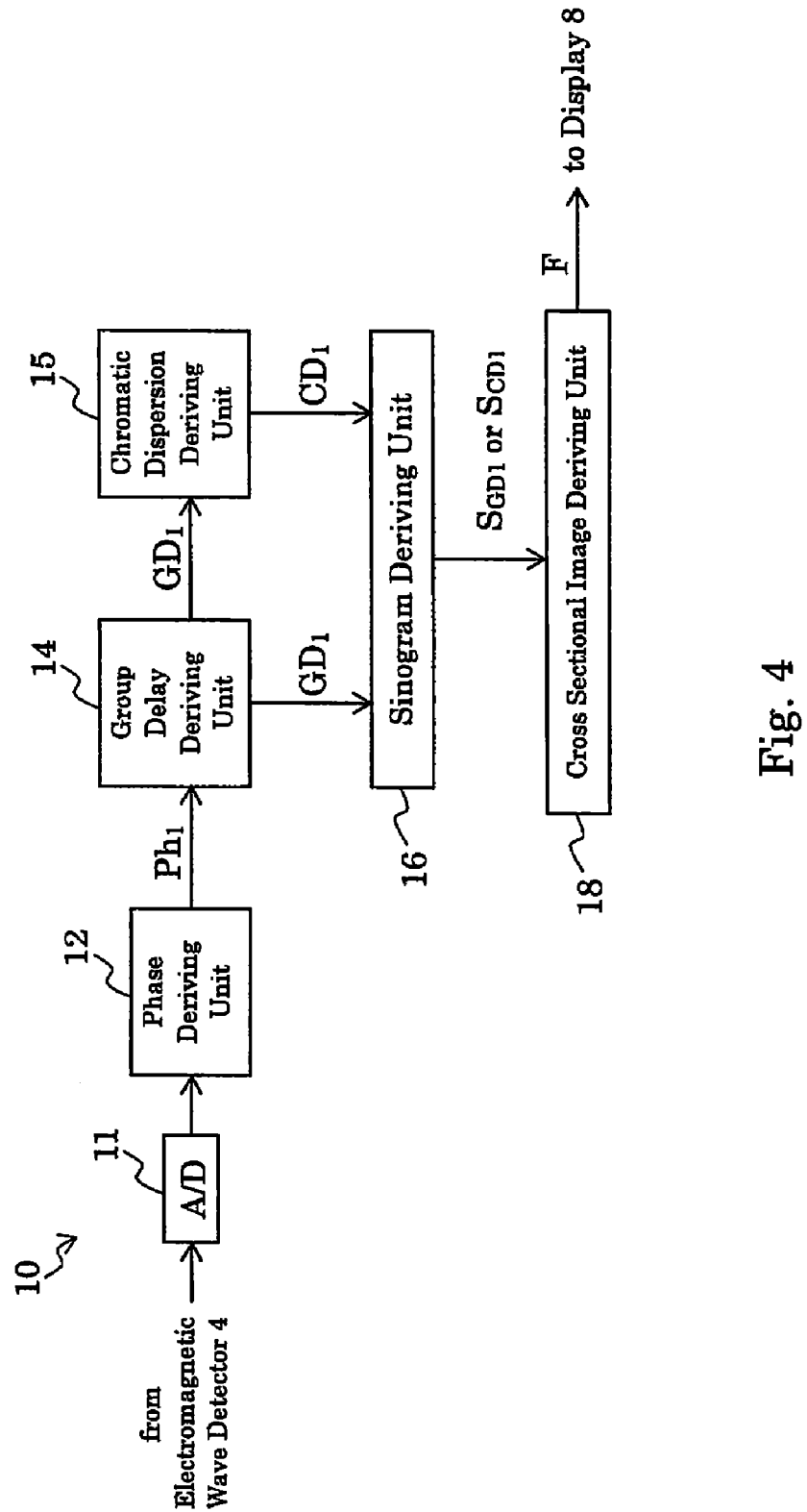
FIG. 4 is a functional block diagram showing a configuration of the image deriving device 10 according to the first embodiment.

FIG. 4 is a functional block diagram showing a configuration of the image deriving device 10 according to the first embodiment. The image deriving device 10 includes an A/D converter 11, a phase deriving unit 12, a group delay deriving unit 14, a chromatic dispersion deriving unit 15, a sinogram deriving unit 16, and a cross sectional image deriving unit (image deriving unit) 18.

The A/D converter 11 converts a detected result by the electromagnetic wave detector 4, which is an analog signal, into a digital signal.

The phase deriving unit 12 derives a phase in the frequency domain of the electromagnetic wave (such as terahertz wave) which has transmitted through the DUT 1 based on the detected result by the electromagnetic wave detector 4.

The phase deriving unit 12 receives the output of the A/D converter 11. The output of the A/D converter 11 is pulse waveform data of the electromagnetic wave which has transmitted through the DUT 1. The pulse waveform data is a function of x (travel in the X direction of the scanning stage 6), θ (travel in the θ direction of the scanning stage 6), and t (time).

The phase deriving unit 12 transforms this pulse waveform data by the Fourier transform, thereby acquiring the spectrum data of the pulse waveform in the frequency domain. The spectrum data of the pulse waveform is a function of x, θ and f (frequency). The phase deriving unit 12 derives a phase $Ph_1(x, \theta, f)$ from the spectrum data of the pulse waveform. It should be noted that arguments (x, θ, f) of the function $Ph_1(x, \theta, f)$ are omitted in FIG. 4. For other function, arguments are omitted similarly.

The group delay deriving unit 14 receives the phase $Ph_1(x, \theta, f)$ from the phase deriving unit 12, and derives a group delay $GD_1(x, \theta, f)$ in the frequency domain of the electromagnetic wave which has transmitted through the DUT 1 based on the phase $Ph_1(x, \theta, f)$.

It should be noted that the group delay $GD_1(x, \theta, f)$ is derived by the group delay deriving unit 14 according to the following equation (1).

$$GD_1(x, \theta, f) = \frac{\partial}{\partial f} Ph_1(x, \theta, f) \qquad \text{Equation (1)}$$

The chromatic dispersion deriving unit 15 derives a chromatic dispersion in the frequency domain of the electromagnetic wave which has transmitted through the DUT 1 based on the derived result by the phase deriving unit 12.

Specifically, the chromatic dispersion deriving unit 15 receives the group delay $GD_1(x, \theta, f)$ from the group delay deriving unit 14, and derives a chromatic dispersion $CD_1(x, \theta, f)$ in the frequency domain of the electromagnetic wave which has transmitted through the DUT 1.

It should be noted that the chromatic dispersion $CD_1(x, \theta, f)$ is represented by the following equation (2), and it is thus recognized that the chromatic dispersion $CD_1(x, \theta, f)$ can be obtained by partially differentiating the group delay $GD_1(x, \theta, f)$ with respect to the frequency f.

It should be noted that the chromatic dispersion deriving unit 15 may receive the phase $Ph_1(x, \theta, f)$ from the phase deriving unit 12, may assign the phase $Ph_1(x, \theta, f)$ to the equation (2), and derives the chromatic dispersion $CD_1(x, \theta, f)$.

$$CD_1(x, \theta, f) = \frac{\partial^2}{\partial f^2} Ph_1(x, \theta, f) \quad \text{Equation (2)}$$

The sinogram deriving unit 16 derives a sinogram based on the derived result (phase $Ph_1(x, \theta, f)$) by the phase deriving unit 12.

Specifically, the sinogram deriving unit 16 receives the group delay $GD_1(x, \theta, f)$ from the group delay deriving unit 14, and derives the sinogram $S_{GD1}(x, \theta)$ for the group delay as shown in the following equation (3). Since the group delay $GD_1(x, \theta, f)$ is derived based on the phase $Ph_1(x, \theta, f)$ (refer to the equation (1)), the sinogram $S_{GD1}(x, \theta)$ is also derived based on the phase $Ph_1(x, \theta, f)$.

$$S_{GD1}(x,\theta) = \int GD_1(x,\theta,f) df \quad \text{Equation (3)}$$

Alternatively, the sinogram deriving unit 16 receives the chromatic dispersion $CD_1(x, \theta, f)$ from the chromatic dispersion deriving unit 15, and derives the sinogram $S_{CD1}(x, \theta)$ for the chromatic dispersion as shown in the following equation (4). Since the chromatic dispersion $CD_1(x, \theta, f)$ is derived based on the phase $Ph_1(x, \theta, f)$ (refer to the equation (2)), the sinogram $S_{CD1}(x, \theta)$ is also derived based on the phase $Ph_1(x, \theta, f)$.

$$S_{CD1}(x,\theta) = \int CD_1(x,\theta,f) df \quad \text{Equation (4)}$$

The cross sectional image deriving unit (image deriving unit) 18 receives the sinogram from the sinogram deriving unit 16, and derives an image of the cross section of the DUT 1 including the intersection 100 based on the sinogram.

When the sinogram derived by the sinogram deriving unit 16 is represented as $S(x, \theta)$, the cross sectional image deriving unit 18 derives an image $F(x,y)$ as described by the following equation (5). The equation (5) implies deriving of the image according to the filtered back projection.

$$F(x, y) = \frac{1}{4\pi} \int_0^{2\pi} \left\{ \frac{1}{2\pi} \int_{-\infty}^{+\infty} \left[ \int_{-\infty}^{+\infty} S(x, \theta) e^{-i\omega x} dx \right] |\omega| e^{i\omega x} d\omega \right\} d\theta \quad \text{Equation (5)}$$

A description will now be given of an operation of the first embodiment.

First, the DUT 1 is fixed to the scanning stage 6. Then, while the scanning stage 6 is moving in the X direction and the Z direction (direction perpendicular to the sheet of FIG. 1) as well as in the $\theta$ direction, the electromagnetic wave output device 2 outputs the electromagnetic wave at a frequency equal to or more than 0.01 [THz] and equal to or less than 100 [THz] (such as a terahertz wave) toward the DUT 1. The terahertz wave output to the DUT 1 transmits through the DUT 1. The electromagnetic wave which has transmitted through the DUT 1 is detected by the electromagnetic wave detector 4. In this way, the DUT 1 is scanned.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_1(x, \theta, f)$ in the frequency domain of the electromagnetic wave which has transmitted through the DUT 1. The group delay $GD_1(x, \theta, f)$ and the chromatic dispersion $CD_1(x, \theta, f)$ are derived based on the phase $Ph_1(x, \theta, f)$, and are fed to the sinogram deriving unit 16.

The sinogram deriving unit 16 derives the sinogram $S_{CD1}(x, \theta)$ based on the group delay, or the sinogram $S_{CD1}(x, \theta)$ based on the chromatic dispersion. The cross sectional image deriving unit 18 derives the image of the cross section of the DUT 1 from the derived sinogram.

The display 8 shows the image derived by the image deriving device 10.

According to the first embodiment, the CT can be carried out not based on the absorption rate of the electromagnetic wave of the DUT 1, but based on the phase $Ph_1(x, \theta, f)$ (specifically the group delay or the chromatic dispersion).

A description will now be given of advantages of the CT based on the group delay or chromatic dispersion.

First, it is assumed that a cross sectional image is obtained by the CT based on the transmission rate (reciprocal of absorption rate) for the DUT 1 which is low in absorption of the terahertz wave. In this case, contrasts (difference in lightness or hue) according to the internal structure of the DUT 1 may not appear in the cross sectional image sufficiently. However, when the CT is carried out based on the group delay or the chromatic dispersion, it is expected that sufficient contrasts appear on a cross sectional image according to the internal structure of the DUT 1. As a result, it is expected that information on the internal structure of the DUT 1 and the like is obtained.

When the refraction index is not uniform in the DUT 1, the terahertz wave does not travel straight in the DUT 1, and is refracted on a refraction boundary. When the optical path of the terahertz wave presents a large curvature due to the refraction, a large power loss is generated on the refraction boundary, the transmission rate decreases, and an error occurs in the CT image based on the transmission rate. On this occasion, the curvature of the optical path of the terahertz wave due to the refraction is determined by the shape of a distribution of the refraction index of the DUT 1. In other words, due to influence of the shape of the distribution of the refraction index of the DUT 1, error occurs in the CT image based on the transmission rate. On the other hand, since the group delay and the chromatic dispersion are independent of the power, the group delay and the chromatic dispersion do not basically change even if the power of the terahertz wave which transmits through the DUT 1 decreases. Thus, the CT image based on the group delay or the chromatic dispersion presents a small error due to the influence of the shape of the distribution of the refraction index of the DUT 1.

Second Embodiment

A second embodiment is different from the first embodiment in that the (first) DUT 1 and a second DUT 20 are used. The DUT 1 according to the first embodiment is referred to as a first DUT 1 according to the second embodiment.

Figure 5:
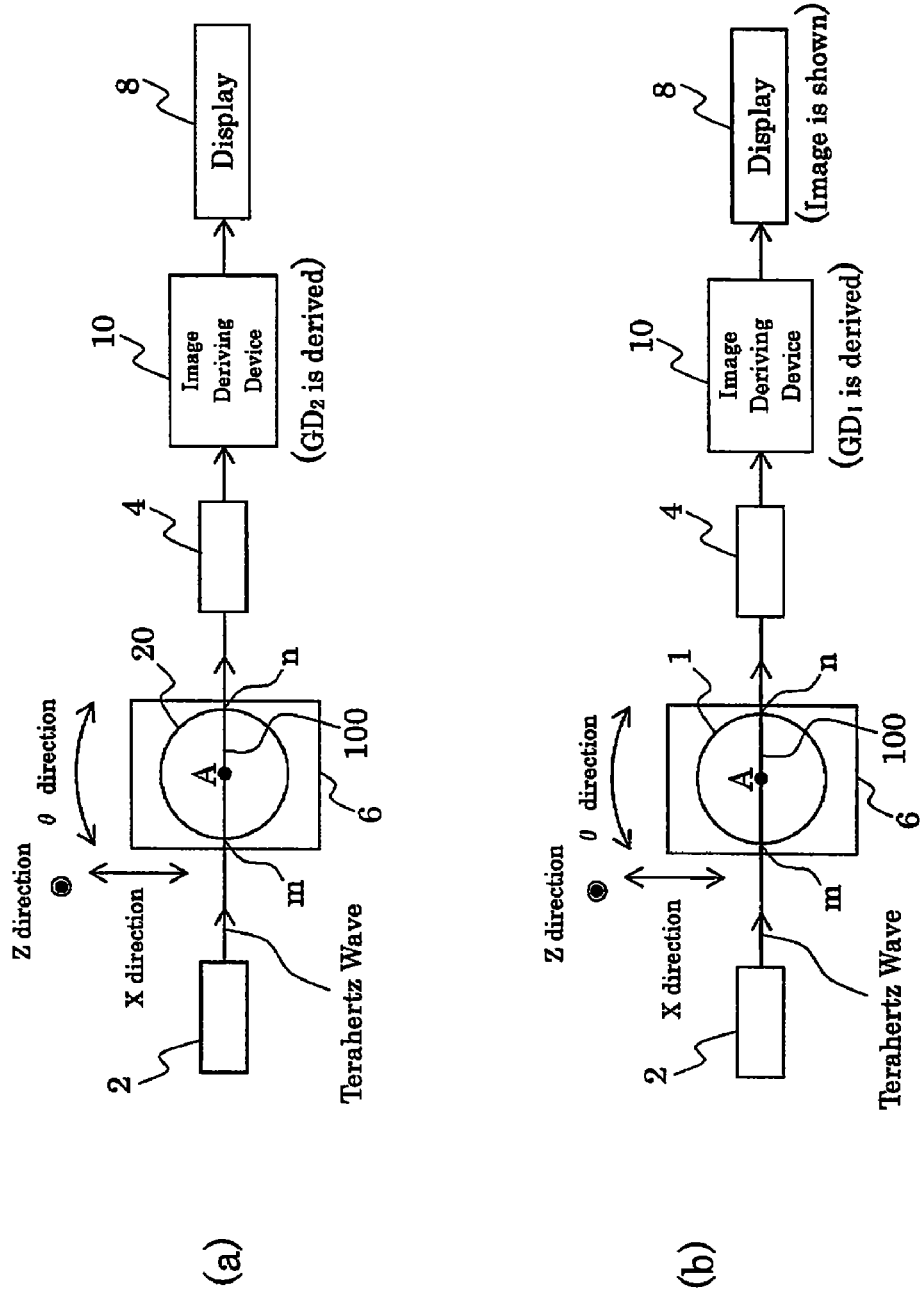
FIGS. 5(a) and 5(b) are diagrams showing a configuration of the electromagnetic wave measurement device according to the second embodiment.
Figure 6:
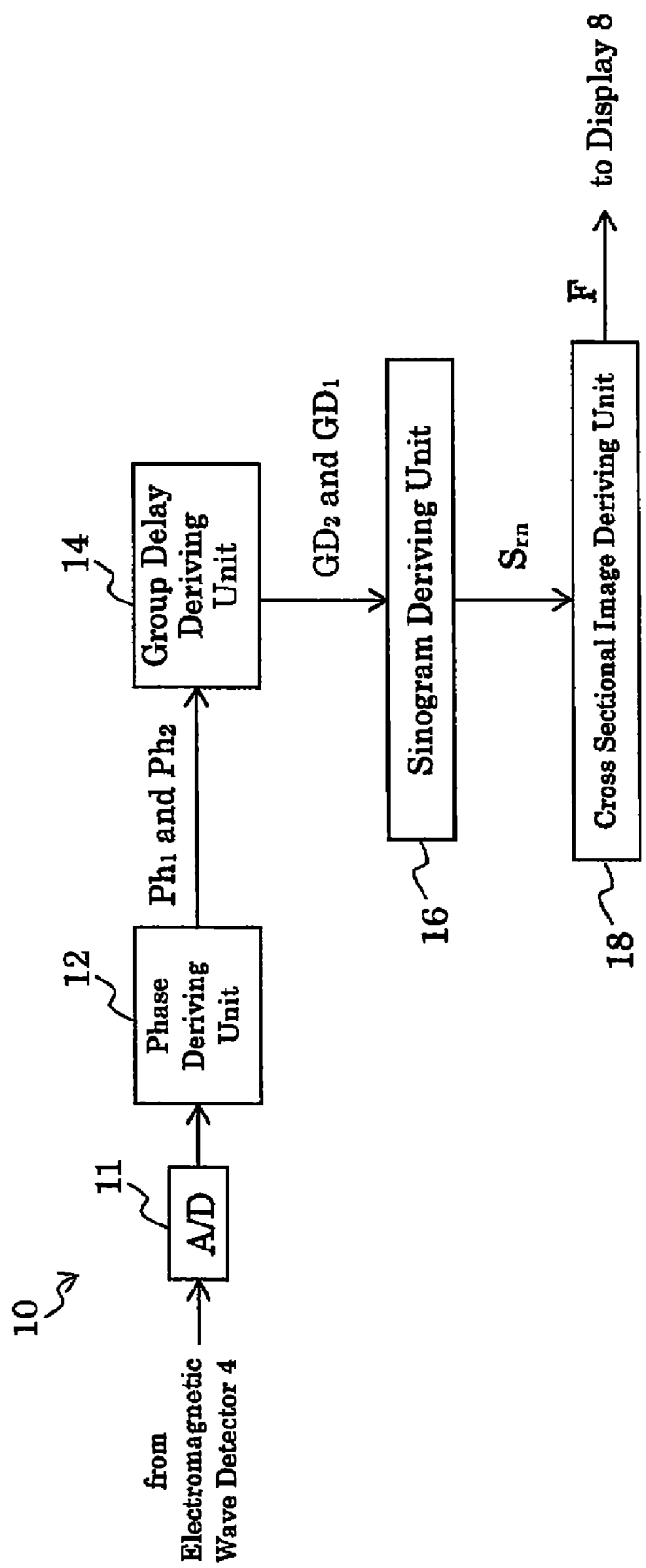
FIG. 6 is a functional block diagram showing a configuration of the image deriving device 10 according to the second embodiment.

FIGS. 5(*a*) and 5(*b*) are diagrams showing a configuration of the electromagnetic wave measurement device according to the second embodiment. FIG. 6 is a functional block diagram showing a configuration of the image deriving device 10 according to the second embodiment.

The configuration of the electromagnetic wave measurement device according to the second embodiment is similar to that of the first embodiment, and hence description thereof is omitted. However, the image deriving device 10 according to the second embodiment is not provided with the chromatic dispersion deriving unit 15. In the following section, the same components are denoted by the same numerals as of the first embodiment, and will be explained in no more details.

A description will now be given of an operation of the second embodiment.

First, the second DUT 20 is fixed to the scanning stage 6 (refer to FIG. 5(*a*)). Then, as in the first embodiment, the scanning of the second DUT 20 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_2(x, \theta, f)$ in the frequency domain of the electromagnetic wave which has transmitted through the second DUT 20. As in the first embodiment, the group delay deriving unit 14 derives, by partially differentiating the phase $Ph_2(x, \theta, f)$ with respect to the frequency f, a second group delay $GD_2(x, \theta, f)$, which is a group delay in the frequency domain of the electromagnetic wave which has transmitted through the second DUT 20.

Then, the first DUT 1 is fixed to the scanning stage 6 (refer to FIG. 5(*b*)). Then, as in the first embodiment, the scanning of the first DUT 1 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_1(x, \theta, f)$ in the frequency domain of the electromagnetic wave which has transmitted through the first DUT 1. As in the first embodiment, the group delay deriving unit 14 derives, by partially differentiating the phase $Ph_1(x, \theta, f)$ with respect to the frequency f, the first group delay $GD_1(x, \theta, f)$, which is a group delay in the frequency domain of the electromagnetic wave which has transmitted through the first DUT 1.

On this occasion, the sinogram deriving unit 16 receives the first group delay $GD_1(x, \theta, f)$ and the second group delay $GD_2(x, \theta, f)$ from the group delay deriving unit 14, and derives a sinogram for a difference in refraction index between the first DUT 1 and the second DUT 20 based on a difference between the first group delay $GD_1(x, \theta, f)$ and the second group delay $GD_2(x, \theta, f)$.

It should be noted that the sinogram $S_{rn}(x, \theta)$ for the difference in refraction index is derived by the sinogram deriving unit 16 according to the following equation (6).

$$S_{rn}(x,\theta)=\int(GD_1(x,\theta,f)-GD_2(x,\theta,f))df \qquad \text{Equation (6)}$$

The cross sectional image deriving unit 18 derives an image of the cross section of the DUT 1 as in the first embodiment.

The display 8 shows the image derived by the image deriving device 10.

According to the second embodiment, the CT can be carried out not based on the absorption rate of the electromagnetic wave of the DUT 1, but based on the phase $Ph_1(x, \theta, f)$ and the phase $Ph_2(x, \theta, f)$ (specifically, the difference between the first group delay and the second group delay).

When the refraction index of the second DUT 20 is known (when the second DUT 20 is air (including nitrogen atmosphere or vacuum), for example), the image can be displayed for the refraction index of the first DUT 1.

In this case, the sinogram deriving unit 16 derives a sinogram $S_n(x, \theta)$ for the refraction index of the first DUT 1 from the sinogram $S_{rn}(x, \theta)$ for the difference in refraction index according to the following equation (7). It should be noted that c is the velocity of light, and $\Delta x$ is space resolution of the sinogram. Moreover, it is assumed that the refraction index of the second DUT 20 is 1. Further, the sinogram $S_{rn}(x, \theta)$ for the difference in refraction index is derived based on the difference between the first group delay $GD_1(x, \theta, f)$ and the second group delay $GD_2(x, \theta, f)$ as described before.

$$S_n(x,\theta)=1+c(S_{rn}(x,\theta))/\Delta x \qquad \text{Equation (7)}$$

The cross sectional image deriving unit 18 derives an image of the cross section of the DUT 1 from the sinogram $S_n(x, \theta)$ for the refraction index of the first DUT 1 as in the first embodiment. The display 8 shows the image derived by the image deriving device 10.

Third Embodiment

Though a third embodiment uses the first DUT 1 and the second DUT 20 as in the second embodiment, it is different from the second embodiment in that the deriving of a sinogram by the sinogram deriving unit 16, and the deriving of an image by the cross sectional image deriving unit 18.

Figure 7:
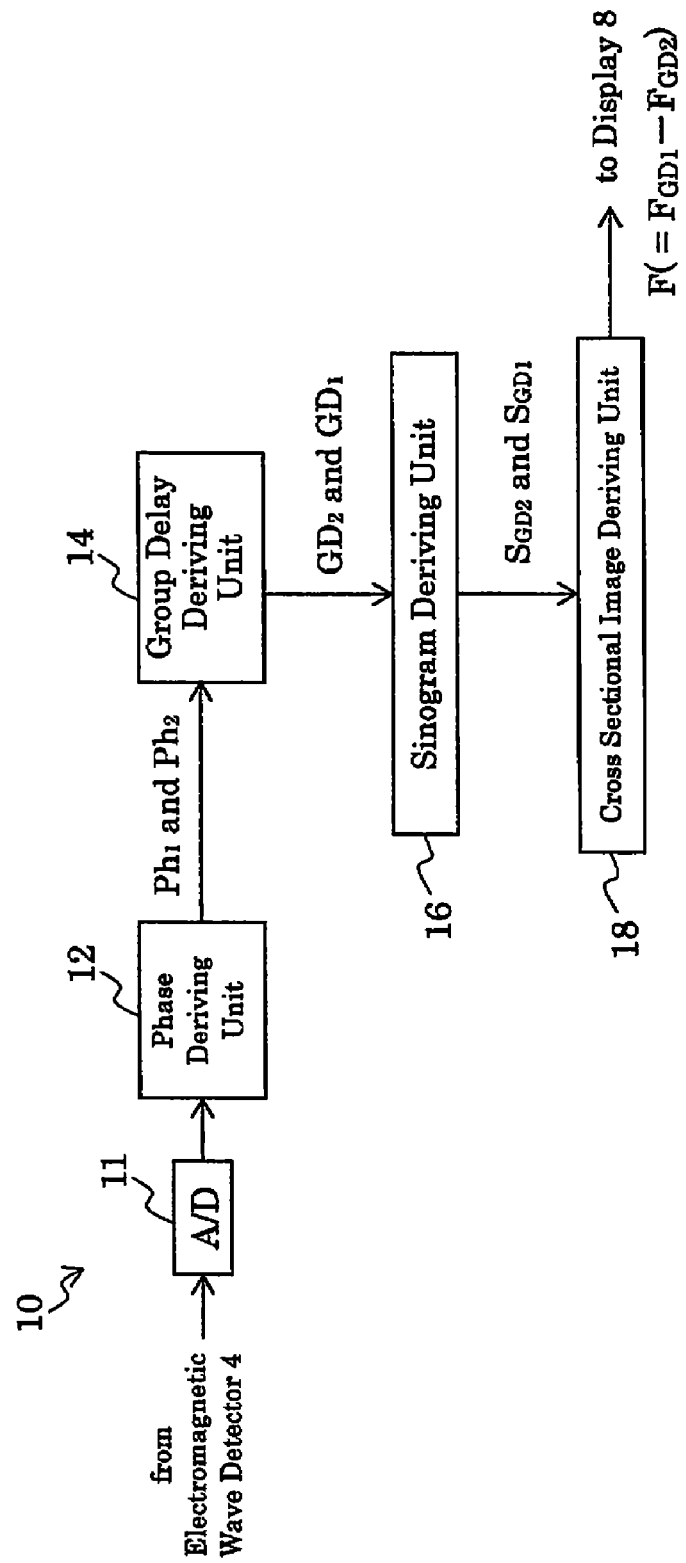
FIG. 7 is a functional block diagram showing a configuration of the image deriving device 10 according to the third embodiment.

FIG. 7 is a functional block diagram showing a configuration of the image deriving device 10 according to the third embodiment.

The configuration of the electromagnetic wave measurement device according to the third embodiment is similar to that of the second embodiment, and hence description thereof is omitted (refer to FIGS. 5(*a*) and 5(*b*)). However, the image deriving device 10 according to the third embodiment is not provided with the chromatic dispersion deriving unit 15. In the following section, the same components are denoted by the same numerals as of the second embodiment, and will be explained in no more details.

A description will now be given of an operation of the third embodiment.

The operation up to the deriving of the second group delay $GD_2(x, \theta, f)$ and the first group delay $GD_1(x, \theta, f)$ is the same as that of the second embodiment.

First, the second DUT 20 is fixed to the scanning stage 6 (refer to FIG. 5(*a*)). Then, as in the first embodiment, the scanning of the second DUT 20 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_2(x, \theta, f)$ in the frequency domain of the electromagnetic wave which has transmitted through the second DUT 20. As in the first embodiment, the group delay deriving unit 14 derives, by partially differentiating the phase $Ph_2(x, \theta, f)$ with respect to the frequency f, the second group delay $GD_2(x, \theta, f)$, which is a group delay in the frequency domain of the electromagnetic wave which has transmitted through the second DUT 20.

Then, the first DUT 1 is fixed to the scanning stage 6 (refer to FIG. 5(*b*)). Then, as in the first embodiment, the scanning of the first DUT 1 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_1(x, \theta, f)$ in the frequency domain of the electromagnetic wave which has transmitted through the first DUT 1. As in the first embodiment, the group delay deriving unit 14 derives, by partially differentiating the phase $Ph_1(x, \theta, f)$ with respect to the frequency f, the first group delay $GD_1(x, \theta, f)$, which is a group delay in the frequency domain of the electromagnetic wave which has transmitted through the first DUT 1.

The operation up to this point is the same as that of the second embodiment.

On this occasion, the sinogram deriving unit 16 receives the first group delay $GD_1(x, \theta, f)$ and the second group delay $GD_2(x, \theta, f)$ from the group delay deriving unit 14, and derives a first sinogram $S_{GD1}(x, \theta)$ based on the first group delay $GD_1(x, \theta, f)$ and a second sinogram $S_{GD2}(x, \theta)$ based on the second group delay $GD_2(x, \theta, f)$.

It should be noted that the first sinogram $S_{GD1}(x, \theta)$ is an integral of the first group delay $GD_1(x, \theta, f)$ with respect to the frequency f. The second sinogram $S_{GD2}(x, \theta)$ is an integral of the second group delay $GD_2(x, \theta, f)$ with respect to the frequency f.

The cross sectional image deriving unit 18 derives an image $F_{GD1}(x,y)$ of the cross section of the first DUT 1 based on the first sinogram $S_{GD1}(x, \theta)$ and an image $F_{GD2}(x,y)$ of the cross section of the second DUT 20 based on the second sinogram $S_{GD2}(x, \theta)$. It should be noted that the method of deriving of the image $F_{GD1}(x,y)$ and the image $F_{GD2}(x,y)$ is the same as that of the first embodiment. In other words, the image $F_{GD1}(x,y)$ and the image $F_{GD2}(x,y)$ can be derived by assigning the first sinogram $S_{GD1}(x, \theta)$ and the second sinogram $S_{GD2}(x, \theta)$ to the sinogram $S(x, \theta)$ in the equation (5).

The cross sectional image deriving unit 18 further derives an image F(x,y) representing a difference in group delay between the first DUT 1 and the second DUT 20 as a difference between the image $F_{GD1}(x,y)$ of the cross section of the first DUT 1 and the image $F_{GD2}(x,y)$ of the cross section of the second DUT 20. It should be noted that $F(x,y)=F_{GD1}(x,y)-F_{GD2}(x,y)$. The image F(x,y) represents the difference in group delay between the first DUT 1 and the second DUT 20 as well as a difference in refraction index between the first DUT 1 and the second DUT 20.

The display 8 shows the image derived by the image deriving device 10.

According to the third embodiment, the CT can be carried out not based on the absorption rate of the electromagnetic wave of the DUT 1, but based on the phase $Ph_1(x, \theta, f)$ and the phase $Ph_2(x, \theta, f)$ (specifically, the first group delay and the second group delay).

Moreover, the above-described embodiment may be realized in the following manner. A computer is provided with a CPU, a hard disk, and a media (such as a floppy disk (registered trade mark) and a CD-ROM) reader, and the media reader is caused to read a medium recording a program realizing the above-described respective components such as the image deriving device 10, thereby installing, the program on the hard disk. This method may also realize the above-described functions.

The invention claimed is:

1. An electromagnetic wave measurement device, comprising:
    an electromagnetic wave output device that outputs an electromagnetic wave, at a frequency equal to or more than 0.01 THz and equal to or less than 100 THz, toward a device under test;
    an electromagnetic wave detector that detects the electromagnetic wave which has transmitted through the device under test;
    a relative position changer that changes a relative position of an intersection at which an optical path of the electromagnetic wave transmitting through the device under test and the device under test intersect, with respect to the device under test;
    a calculator that calculates, based on an electromagnetic wave detected by the electromagnetic wave detector, a phase in a frequency domain of the electromagnetic wave which has transmitted through the device under test;
    a sinogram generator that generates a sinogram based on a result calculated by the calculator; and
    an image generator that generates, based on the sinogram, an image of a cross section of the device under test including the intersection, the image generator comprising a group delay generator that generates, based on the result calculated by the calculator, a group delay in the frequency domain of the electromagnetic wave which has transmitted through the device under test,
    wherein the sinogram generator generates the sinogram for the group delay.

2. An electromagnetic wave measurement device, comprising:
    an electromagnetic wave output device that outputs an electromagnetic wave, at a frequency equal to or more than 0.01 THz and equal to or less than 100 THz, toward a device under test;
    an electromagnetic wave detector that detects the electromagnetic wave which has transmitted through the device under test;
    a relative position changer that changes a relative position of an intersection at which an optical path of the electromagnetic wave transmitting through the device under test and the device under test intersect, with respect to the device under test;
    a calculator that calculates, based on an electromagnetic wave detected by the electromagnetic wave detector, a phase in a frequency domain of the electromagnetic wave which has transmitted through the device under test;
    a sinogram generator that generates a sinogram based on a result calculated by the calculator; and
    an image generator that generates, based on the sinogram, an image of a cross section of the device under test including the intersection, the image generator comprising a chromatic dispersion generator that generates, based on the result calculated by the calculator, a chromatic dispersion in the frequency domain of the electromagnetic wave which has transmitted through the device under test,
    wherein the sinogram generator generates the sinogram for the chromatic dispersion.

3. An electromagnetic wave measurement device, comprising:
    an electromagnetic wave output device that outputs an electromagnetic wave, at a frequency equal to or more than 0.01 THz and equal to or less than 100 THz, toward a device under test;
    an electromagnetic wave detector that detects the electromagnetic wave which has transmitted through the device under test;
    a relative position changer that changes a relative position of an intersection at which an optical path of the electromagnetic wave transmitting through the device under test and the device under test intersect, with respect to the device under test;
    a calculator that calculates, based on an electromagnetic wave detected by the electromagnetic wave detector, a phase in a frequency domain of the electromagnetic wave which has transmitted through the device under test;

a sinogram generator that generates a sinogram based on a result calculated by the calculator; and an image generator that generates, based on the sinogram, an image of a cross section of the device under test including the intersection, wherein the device under test comprises a first device under test and a second device under test, the image generator comprising a group delay generator that generates, based on the result calculated by the calculator, a first group delay in the frequency domain of the electromagnetic wave which has transmitted through the first device under test, and a second group delay in the frequency domain of the electromagnetic wave which has transmitted through the second device under test, and wherein the sinogram generator generates the sinogram for a difference in refraction index between the first device under test and the second device under test based on a difference between the first group delay and the second group delay.

4. The electromagnetic wave measurement device according to claim 3, wherein:

the refraction index of the second device under test is known; and the sinogram generator generates the sinogram for the refraction index of the first device under test based on a difference between the first group delay and the second group delay.

5. An electromagnetic wave measurement device, comprising:

an electromagnetic wave output device that outputs an electromagnetic wave, at a frequency equal to or more than 0.01 THz and equal to or less than 100 THz, toward a device under test;

an electromagnetic wave detector that detects the electromagnetic wave which has transmitted through the device under test;

a relative position changer that changes a relative position of an intersection at which an optical path of the electromagnetic wave transmitting through the device under test and the device under test intersect, with respect to the device under test;

a calculator that calculates, based on an electromagnetic wave detected by the electromagnetic wave detector, a phase in a frequency domain of the electromagnetic wave which has transmitted through the device under test;

a sinogram generator that generates a sinogram based on a result calculated by the calculator; and an image generator that generates, based on the sinogram, an image of a cross section of the device under test including the intersection, wherein the device under test comprises a first device under test and a second device under test, the image generator comprising a group delay generator that generates, based on the result calculated by the calculator, a first group delay in the frequency domain of the electromagnetic wave which has transmitted through the first device under test, and a second group delay, in the frequency domain of the electromagnetic wave which has transmitted through the second device under test wherein:

the sinogram generator generates a first sinogram based on the first group delay and a second sinogram based on the second group delay; and the image generator generates an image of a cross section of the first device under test based on the first sinogram, and an image of a cross section of the second device under test based on the second sinogram, and, as a difference between the image of the cross section of the first device under test and the image of the cross section of second device under test, derives an image representing a difference in group delay between the first device under test and the second device under test.

6. An electromagnetic wave measurement method, comprising:

outputting an electromagnetic wave, at a frequency equal to or more than 0.01 THz and equal to or less than 100 THz, toward a device under test;

detecting the electromagnetic wave which has transmitted through the device under test;

changing a relative position of an intersection at which an optical path of the electromagnetic wave transmitting through the device under test and the device under test intersect, with respect to the device under test;

calculating based on an electromagnetic wave detected by the detecting, a phase in a frequency domain of the electromagnetic wave which has transmitted through the device under test;

generating a sinogram based on a result of the calculation; and generating, based on the sinogram, an image of a cross section of the device under test including the intersection, the image generating comprising generating, based on the result of the calculation, a group delay in the frequency domain of the electromagnetic wave which has transmitted through the device under test, wherein the sinogram generating generates the sinogram for the group delay.

7. An electromagnetic wave measurement method, comprising:

an electromagnetic wave output device that outputs an electromagnetic wave, at a frequency equal to or more than 0.01 THz and equal to or less than 100 THz, toward a device under test;

detecting the electromagnetic wave which has transmitted through the device under test;

changing a relative position of an intersection at which an optical path of the electromagnetic wave transmitting through the device under test and the device under test intersect, with respect to the device under test;

calculating, based on an electromagnetic wave detected by the detecting, a phase in a frequency domain of the electromagnetic wave which has transmitted through the device under test;

generating a sinogram based on a result of the calculation; and generating, based on the sinogram, an image of a cross section of the device under test including the intersection the image generating comprising generating a chromatic dispersion, based on the result of the calculation, in the frequency domain of the electromagnetic wave which has transmitted through the device under test, wherein generating the sinogram generates the sinogram for the chromatic dispersion.

8. An electromagnetic wave measurement method, comprising:

outputting an electromagnetic wave, at a frequency equal to or more than 0.01 THz and equal to or less than 100 THz, toward a device under test;

detecting the electromagnetic wave which has transmitted through the device under test;
changing a relative position of an intersection at which an optical path of the electromagnetic wave transmitting through the device under test and the device under test intersect, with respect to the device under test;
calculating, based on an electromagnetic wave detected by the detecting, a phase in a frequency domain of the electromagnetic wave which has transmitted through the device under test;
generating a sinogram based on a result of the calculation; and
generating, based on the sinogram, an image of a cross section of the device under test including the intersection,
wherein the device under test comprises a first device under test and a second device under test, the image generating comprises generating, based on the result of the calculating, a first group delay in the frequency domain of the electromagnetic wave which has transmitted through the first device under test, and a second group delay in the frequency domain of the electromagnetic wave which has transmitted through the second device under test,
wherein the sinogram generating generates the sinogram for a difference in refraction index between the first device under test and the second device under test based on a difference between the first group delay and the second group delay.

9. An electromagnetic wave measurement method, comprising:
outputting an electromagnetic wave, at a frequency equal to or more than 0.01 THz and equal to or less than 100 THz, toward a device under test;
detecting the electromagnetic wave which has transmitted through the device under test;
changing a relative position of an intersection at which an optical path of the electromagnetic wave transmitting through the device under test and the device under test intersect, with respect to the device under test;
calculating, based on an electromagnetic wave detected by the detecting, a phase in a frequency domain of the electromagnetic wave which has transmitted through the device under test;
generating a sinogram based on a result of the calculation; and
generating, based on the sinogram, an image of a cross section of the device under test including the intersection,
wherein the device under test comprises a first device under test and a second device under test, the image generating comprising generating, based on the result of the calculation, a first group delay in the frequency domain of the electromagnetic wave which has transmitted through the first device under test, and a second group delay in the frequency domain of the electromagnetic wave which has transmitted through the second device under test wherein:
the sinogram generating generates a first sinogram based on the first group delay and a second sinogram based on the second group delay; and
the image generating comprising generating an image of a cross section of the first device under test based on the first sinogram, and an image of a cross section of the second device under test based on the second sinogram, and, as a difference between the image of the cross section of the first device under test and the image of the cross section of second device under test, generating an image representing a difference in group delay between the first device under test and the second device under test.

10. The electromagnetic wave measurement method according to claim 8, wherein the refraction index of the second device under test is known and generating the sinogram comprises generating a sinogram for the refraction index of the first device under test based on the difference between the first group delay and the second group delay.

* * * * *